(12) United States Patent
Strutz et al.

(10) Patent No.: US 9,394,218 B2
(45) Date of Patent: Jul. 19, 2016

(54) MANUFACTURE OF METHYLOLALKANES

(71) Applicant: Oxea Bishop LLC, Dallas, TX (US)

(72) Inventors: Heinz Strutz, Moers (DE); Donald K. Raff, Waynesville, NC (US); Guido D. Frey, Mülheim (DE); Norman Nowotny, Essen (DE); Marcos Schroeder, Andover, KS (US); Fred Gaytan, Kingsville, TX (US); Tracy Kevin Hung, Corpus Christi, TX (US); William E. Slinkard, Richmond, TX (US)

(73) Assignee: OXEA BISHOP LLC, Dallas, TX (US)

( * ) Notice: Subject to any disclaimer, the term of this patent is extended or adjusted under 35 U.S.C. 154(b) by 0 days.

(21) Appl. No.: 14/903,619

(22) PCT Filed: Jul. 23, 2014

(86) PCT No.: PCT/US2014/047738
§ 371 (c)(1),
(2) Date: Jan. 8, 2016

(87) PCT Pub. No.: WO2015/020796
PCT Pub. Date: Feb. 12, 2015

(65) Prior Publication Data
US 2016/0145179 A1    May 26, 2016

Related U.S. Application Data

(60) Provisional application No. 61/862,574, filed on Aug. 6, 2013.

(51) Int. Cl.
| | |
|---|---|
| C07C 29/38 | (2006.01) |
| C07C 31/22 | (2006.01) |
| B01J 19/00 | (2006.01) |
| B01J 19/24 | (2006.01) |
| B01F 5/06 | (2006.01) |

(52) U.S. Cl.
CPC .............. *C07C 29/38* (2013.01); *B01F 5/0615* (2013.01); *B01J 19/006* (2013.01); *B01J 19/242* (2013.01); *B01J 19/2405* (2013.01); *B01F 2005/0633* (2013.01); *B01F 2005/0637* (2013.01); *B01J 2219/0004* (2013.01); *B01J 2219/0006* (2013.01); *B01J 2219/00094* (2013.01); *B01J 2219/00159* (2013.01); *B01J 2219/00204* (2013.01); *B01J 2219/00238* (2013.01); *B01J 2219/00772* (2013.01); *B01J 2219/00777* (2013.01); *B01J 2219/24* (2013.01)

(58) Field of Classification Search
CPC ........ C07C 29/38; B01J 19/00; B01J 2219/00
USPC .......................................... 568/853; 422/641
See application file for complete search history.

(56) References Cited

U.S. PATENT DOCUMENTS

| | | |
|---|---|---|
| 3,183,274 A | 5/1965 | Robeson |
| 5,603,835 A | 2/1997 | Cheung et al. |
| 5,948,943 A | 9/1999 | Supplee et al. |
| 7,253,326 B1 | 8/2007 | Eom et al. |
| 7,301,058 B2 | 11/2007 | Wartini et al. |
| 8,354,561 B2 | 1/2013 | Windhorst et al. |

FOREIGN PATENT DOCUMENTS

| | | |
|---|---|---|
| DE | 1154080 B | 9/1963 |
| DE | 10234016 A1 | 2/2004 |
| EP | 2457648 A1 | 5/2012 |

OTHER PUBLICATIONS

International Search Report dated Dec. 22, 2014.
Richard L. Shilling, "Selecting Tube Inserts for Shell-and-Tube Heat Exchangers", Chemical Engineering Progress, Sep. 2012, pp. 19-25, American Institute of Chemical Engineers, New York, NY.

*Primary Examiner* — Sikarl Witherspoon
(74) *Attorney, Agent, or Firm* — Michael W. Ferrell

(57) ABSTRACT

A multistage tubular reaction system and method for preparing methylol derivatives of an aldehyde includes a tubular reaction system with a plurality of successive reactor stages provided with a formaldehyde containing feed stream. The system includes multiple feed ports for the staged addition of $C_2$ or higher condensible aldehyde and/or base to the formaldehyde containing stream at a plurality of successive feed points to provide a production stream, which is progressively provided with additional reactants as the production stream advances through the successive reaction stages. Advantages include better temperature control and reduced byproduct formation.

16 Claims, 3 Drawing Sheets

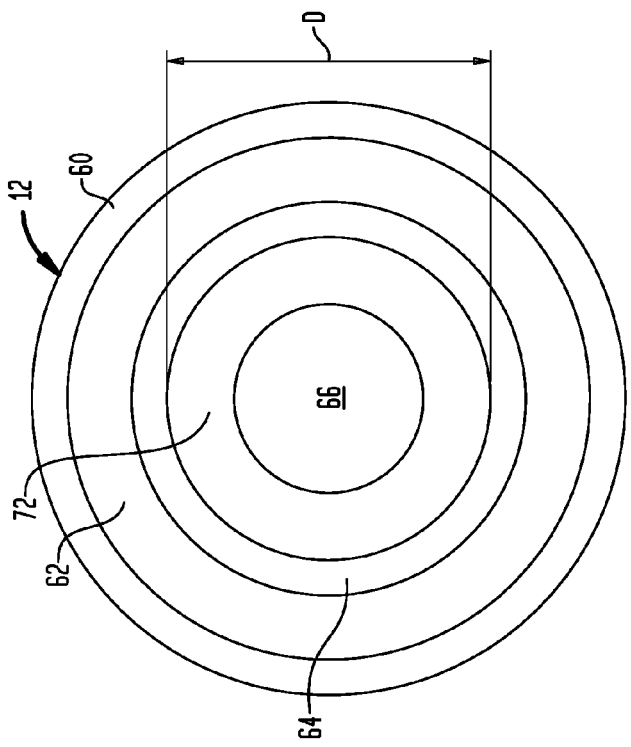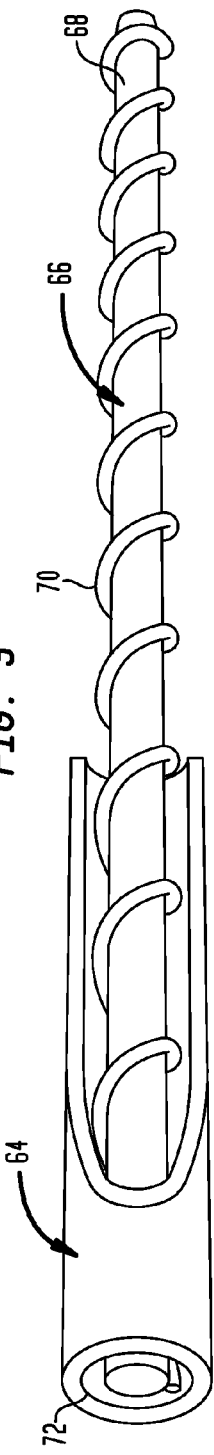

MANUFACTURE OF METHYLOLALKANES

CLAIM FOR PRIORITY

This application is based International Application no. PCT/US2014/047738 FILED Jul. 23, 2014 entitled IMPROVED MANUFACTURE OF METHYLOLALKANES which was based on U.S. Provisional Application No. 61/862,574 filed Aug. 6, 2013, the priorities of which are hereby claimed and the disclosures of which are incorporated herein by reference.

TECHNICAL FIELD

The present invention relates to improved manufacture of methylolalkanes such as trimethylolpropane (TMP) by way of multistage reaction in a tubular reactor with a plurality of tube banks. Staged addition of reactant aldehyde and/or base promotes better temperature control and reduces unwanted byproducts such as 2-ethylhexyl dimers, methylolalkane formals, methanol and so forth.

BACKGROUND

Manufacture of methylolalkanes is carried out in a variety of processes including by the reaction of formaldehyde with another aldehyde condensible with formaldehyde (hereinafter sometimes referred to as reactant aldehyde), that is, an aldehyde having at least one hydrogen bound at the α-carbon atom adjacent to the carbonyl moiety. The base-catalyzed aldol reaction of the reactant aldehyde with formaldehyde initially generates the methylol derivative of the aldehyde in the first reaction step. Then the aldehyde moiety may be converted in a second reaction step by reaction with further formaldehyde and base in a Cannizzaro-reaction into an alcohol group. Simultaneously, the formate of the base is generated. The $1^{st}$ reaction step, the aldol reaction, and the $2^{nd}$ reaction step, a Cannizzaro reaction, may either be carried out separately or in one working step. The bases used both for the base catalyzed reaction step 1 and also for the reaction step 2 which is stoichiometric in relation to the base quantity may optionally each independently be, for example, alkali metal or alkaline earth metal hydroxides, carbonates, or tertiary amines. In the so-called inorganic Cannizzaro process, an inorganic base is used, such as sodium hydroxide, potassium hydroxide or calcium hydroxide. The resultant formates, such as potassium formate or calcium formate can be used in further industrial applications such as an assistant in the leather industry.

The reactions of formaldehyde with acetaldehyde, propionaldehyde, n-butyraldehyde and isobutyraldehyde are of particular interest. The corresponding reaction products are pentaerythritol, trimethylolethane, trimethylolpropane and neopentylglycol. These are polyhydric alcohols of great industrial significance which find use, for example, in the field of coating resins, powder coating, foam production and polyester production.

In particular, the manufacture of TMP according to the inorganic Cannizzarro process is disclosed, for example, in U.S. Pat. Nos. 3,183,274, 5,948,943, 7,253,326 and 8,354,561. Batchwise production of TMP is seen in U.S. Pat. No. 7,253,326 to Eom et al., wherein the batch production is followed by a semi-continuous product recovery train. While batchwise production may be advantageous in terms of raw material use, such systems are relatively difficult to operate and capital costs are higher than continuous systems.

TMP is prepared from n-butyraldehyde and formaldehyde. In one preferred process, base-catalyzed aldol reaction initially generates 2,2-dimethylolbutyraldehyde in a first reaction step which is then converted to a TMP-formate mixture by way of a Cannizzaro reaction. The TMP-containing mixture is typically extracted with an organic solvent, such as ethyl acetate, thereby providing an organic phase comprising TMP and an aqueous phase containing the formate. The solvent is separated and the crude TMP is purified by distillation. Typical processing is seen in U.S. Pat. No. 5,603,835 to Cheung et al., Comparative Example 1, Col. 7. See, also, U.S. Pat. No. 5,948,943 to Supplee et al. referred to above.

The reaction of the aldehyde with formaldehyde is highly exothermic and can result in excessively high temperatures in the reaction zone before the heat can be removed. The temperature spikes lead to efficiency losses due to side reactions. In order to reduce said temperature spikes, the art generally teaches to use a relatively dilute aqueous formaldehyde solution and aqueous solution of the inorganic base in order to moderate temperature. Because of the presence of large amounts of water in the reaction mixture, the heat capacity is relatively high so that the exothermic heat of the reaction does not raise the temperature of the mixture to a level above the desired range.

Besides the large amount of water, it is conventionally typical to use formaldehyde in substantial excess over the theoretical amount based on the reactant aldehyde. In cases where n-butyraldehyde is reacted with formaldehyde to produce trimethylolpropane the art teaches generally a formaldehyde excess of about 1 to 7 moles or so over the formaldehyde needed for the actual reaction.

Commonly, the aqueous formaldehyde solution is blended with the starting aldehyde continuously to produce a stream of aqueous mixed aldehydes and the aqueous solution of the inorganic base is injected into this stream in a mixing zone. The reaction mixture is then fed to a reaction zone. Heat generation is most problematical at or near the mixing zone where the reactants are most highly concentrated. Heat generated in these areas leads to temperature spikes and byproduct generation. As will be appreciated from the foregoing references, byproducts can cause color and other product quality problems, leading to higher purification expense in addition to loss of efficiency because of lower yields. Moreover, large amounts of water needed as a temperature moderator are difficult and expensive to process.

SUMMARY OF INVENTION

In connection with methylolalkane manufacture, byproducts can be reduced significantly if the reaction of the aqueous formaldehyde, a $C_2$ or higher condensible aldehyde and the aqueous solution of the inorganic base are conducted in a tube reactor where the reactants are added in stages at various tubes up to the required amount. So also, heat generation is less localized and better temperature regulation is achieved. Optionally, tube inserts are used to promote heat transfer and mixing, preferably proximate a plurality of feed ports. Various configurations and types of tube inserts are commercially available from Koch Heat Transfer Company and their use is discussed in Chemical Engineering Process, September 2012, pages 19-25; Shilling, Richard, L.; the disclosure of which is incorporated herein by reference.

The tube reactor according to another aspect of the invention comprises a series n of tubes and each series contains m single tubes, where m can vary between reactor stages. The staged addition of the reactants in accordance with the invention occurs at various locations and preferably in the first tube of a series of tubes. In particular the aldehyde and the aqueous solution of the inorganic base are added to the various stages while the aqueous formaldehyde solution flows through the tube reactor.

The tube reactor is designed as a double-pipe reactor with the reaction zone in the inner tube and a coolant in the outer tube, sometimes referred to herein as a jacketed construction as discussed hereinafter.

Further details and advantages will become apparent from the discussion which follows.

DESCRIPTION OF DRAWINGS

The invention is described in detail below in connection with numerous examples and in connection with the attached FIGS. In the FIGS:

FIG. 2 is a schematic sectional view of a reactor tube with a tube insert residing in a cooling conduit;

FIG. 3 is a view in perspective of a section of reactor tube provided with a wire-wrapped displacement insert;

DETAILED DESCRIPTION

Figure 1:
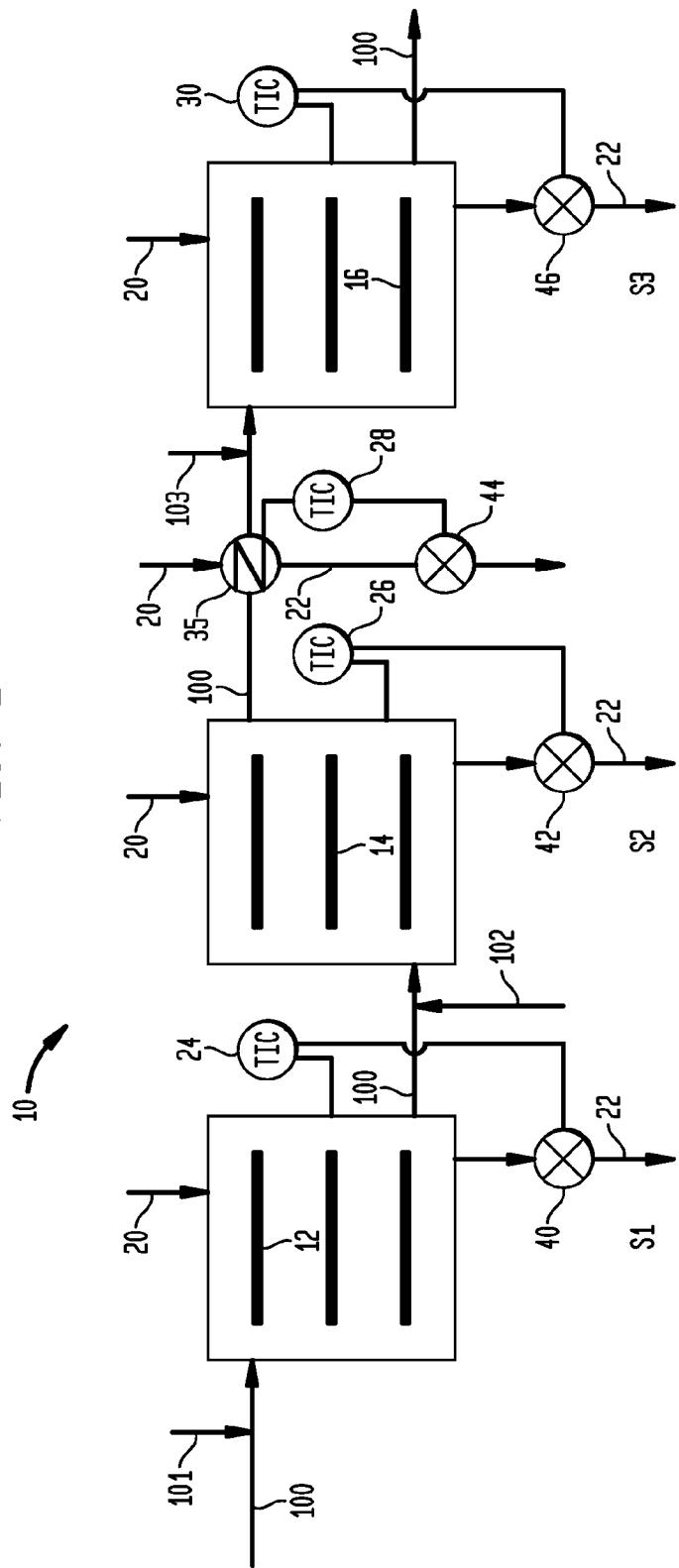
FIG. 1 is a schematic diagram illustrating the inventive process employing a tube reactor with the staged addition of n-butyraldehyde and an aqueous solution of potassium hydroxide wherein each series of tubes has a temperature indication controller which is used to control a valve manipulating the cooling flow through that series depending on the heat of reaction generated in that series.

The invention is described in detail below in connection with the FIGS. for purposes of illustration, only. The invention is defined in the appended claims. Terminology used throughout the specification and claims herein is given its ordinary meaning as supplemented by the discussion immediately below.

"Aggregate" and like terminology refers to the total amount of reactants or material added to the reaction system by adding the amounts supplied to each stage. For example, the aggregate amount of reactant aldehyde added to the system includes the sum of the amounts supplied at each stage.

A $C_2$ or higher condensible aldehyde is a two carbon or more carbon aldehyde which will undergo condensation with formaldehyde to form a methylol derivative of that aldehyde. Aldehydes condensible with formaldehyde have at least one hydrogen bound at the α-carbon atom adjacent to the carbonyl moiety. Useful higher aldehydes are virtually all alkanals having an acidic hydrogen atom in the α-position to the carbonyl group. Aliphatic aldehydes having from 2 to 24 carbon atoms may be used as starting materials and may be straight-chain or branched or else contain alicyclic groups. Equally, araliphatic aldehydes are suitable as starting materials, provided that they contain at least one hydrogen in the α-position to the carbonyl group. In general, aralkyl aldehydes having from 8 to 24 carbon atoms, preferably from 8 to 12 carbon atoms, are used as starting materials, for example phenyl acetaldehyde. Preference is given to aliphatic aldehydes having from 2 to 12 carbon atoms. Especially preferred $C_2$ or higher condensible aldehydes include acetaldehyde, propionaldehyde, n-butyraldehyde and isobutyraldehyde.

Unwanted byproducts avoided in accordance with the invention include dimers such as 2-ethylhexyl dimers produced by self-aldol condensation of butyraldehyde and may include a plurality of impurities believed derived from reaction of monomethylol compounds such as monomethylol butyraldehyde. Such impurities include for, example, monocyclic TMP-formal (MCF):

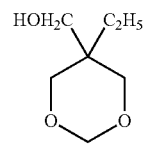

monolinear bis-TMP-formal (MBLF or TMP-BMLF):

Methyl-(monolinear)TMP-formal:

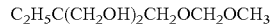

and di-TMP:

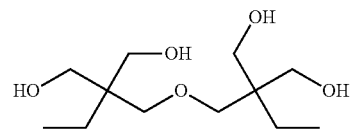 [SMILES: CCC(CO)(CO)COCC(CC)(CO)CO]

2[2,2-bis(hydroxymethyl)butoxymethyl]-2-ethylpropane-1,3-diol

In a process including a Cannizzaro process, staging base addition also reduces unwanted methanol generation which increases raw material efficiency.

As used herein, a Cannizzaro process refers to methyloalkane synthesis where the condensate intermediate is reacted with additional formaldehyde and base to yield the corresponding methylolalkane, for example, a Cannizzaro TMP synthesis as shown in the following scheme:

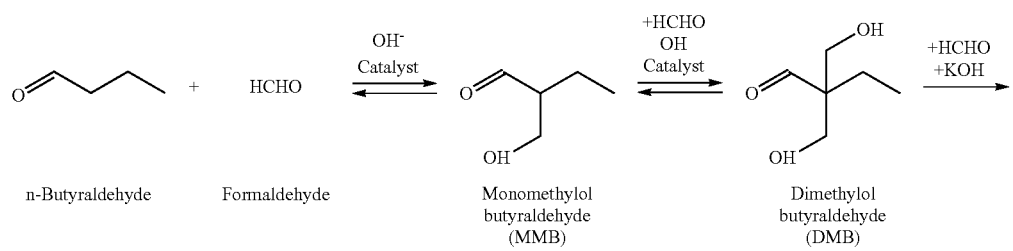

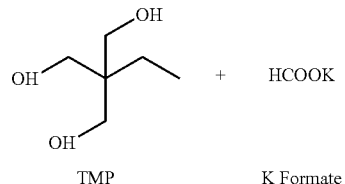

TMP     K Formate

"Tube insert" and like terminology refers to a part disposed in a reaction tube to enhance mixing and heat transfer. A tube insert may be a static mixer insert, a boundary layer interrupter insert, a swirl flow insert, a displaced flow insert or a combination of these types of inserts. Particularly preferred is a wire-wrapped displacement flow insert which combines swirl flow and displacement flow augmentation. Displaced-flow inserts increase heat transfer by blocking flow furthest from the tube wall and increasing the Reynolds number of the liquid and therefore the U-value of the system. In connection with the present invention, it also extends the area in which the reaction is occurring, which, in turn, reduces the final peak temperature seen in the reactor by increasing the amount of area used for heat transfer in critical areas. By using a wire-wrapped tube insert, some swirl flow is induced as well, which imparts a helical flow path which further increases the mixing and turbulence at the wall, which may be operable to change flow from a laminar operation to a turbulent operation in that tube, depending upon conditions. In preferred embodiments employing displaced flow inserts, the ratio of $D/D_e$ (defined below) is from 1.5 to 3. In the most preferred embodiments, inserts are used in selected sections of reactor pipe only so as not to overtax the feed pumps of the reaction system.

"Heat transfer equivalent diameter" or $D_e$ is defined by the relationship:

$$De = \frac{4Nfa}{\pi D}$$

where Nfa is the net free area inside of the tube and D is the (inside) diameter of the tube.

"Methylol derivative" and like terminology refers to condensation products of formaldehyde and aldehydes condensible with formaldehyde as well as the corresponding polyol end products formed by reduction of the condensation product with formaldehyde or hydrogenation. Methylol derivatives include methylolalkanes and methylolaldehydes.

"Proximate" refers to closeness in position of a feed port and generally means that a feed point is proximate to a reactor tube section with a tube insert if less than 30% of added reactant aldehyde reacts over a reactor length prior to entry into the reactor tube section with a tube insert or if the feed point is at a distance of less than 6 meters from the reactor tube section with a tube insert. In preferred embodiments, a proximate feed point is within a distance of 6 meters of a reactor tube section with a tube insert and still more preferably a proximate feed point is within a distance of 5 meters of a reactor tube section with a tube insert. In many cases a proximate feed point is within a distance of 3 meters of a reactor tube section with a tube insert.

A "stage" of a multistage reaction system is a portion of the reactor system discretely configured with respect to other stages by way of an additional feed port for reactants or catalyst or independent temperature control of the stage, or by way of a separate flow of cooling medium to the stage.

"Successive" refers to a serial arrangement of reactor stages, for example, where later reaction stages are downstream of initial stages as is seen in FIG. 1.

Referring to FIG. 1, there is illustrated schematically a reaction system 10 comprising multiple banks or stages S1, S2, S3 and so forth of reaction tubes such as tubes indicated at 12, 14, 16 and so forth. Each bank preferably has multiple tubes connected in series within each bank as shown schematically. 3,4,5,6 or more stages may be employed, each having 3-10 tubes in series if so desired. Stages without additional reactant feed may be interposed between stages receiving fresh charges of reactants.

Reaction system 10 also includes a cooling system which includes a plurality of coolant feeds 20 for providing coolant to the reaction tubes and a plurality of return lines 22 for returning coolant to the cooling system. Also provided are a plurality of temperature indicator controllers 24, 26, 28, 30, a cooler 35, and a plurality of control valves indicated at 40, 42, 44, and 46.

The reaction tubes are connected in series as indicated schematically and have the structure generally illustrated in FIGS. 2 and 3, although only the tubes receiving a fresh charge of aldehyde reactant need be provided with a tube insert to enhance mixing and heat transfer. Likewise, reactor stages without additional reactant feed may include inlet tubes without tube inserts since the stream concentration profiles are already relatively well developed.

Referring to FIGS. 2 and 3, there is shown reaction tube 12, which has an outer shell 60, and annular cooling channel 62 and an inner reaction tube 64 which is provided with a tube insert 66. The reaction tube has an inside diameter, D. Preferably, insert 66 is a wire-wrapped cylinder, a combination swirl flow and displacement insert which reduces residence time in the areas where reactants are introduced and heat transfer is most critical.

Insert 66 thus has a cylindrical body 68, a wire wrap 70 and resides in reaction tube 64 as shown in FIG. 3. The net free area 72 is thus defined between insert 66 and the inner wall of tube 64.

The reaction tubes in system 10 without inserts are of the same general configuration, but the inner channel is unrestricted.

In preferred cases, the reaction tubes with inserts have a ratio of D/De of from 1.5 to 3 as noted above.

Figure 4:
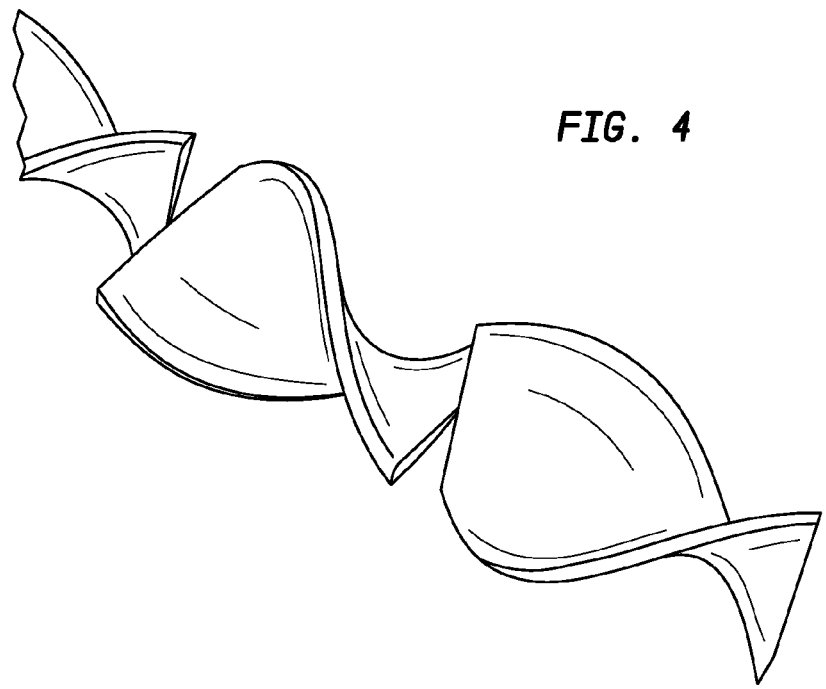
FIG. 4 is a view in perspective of a static mixer tube insert.
Figure 5A:
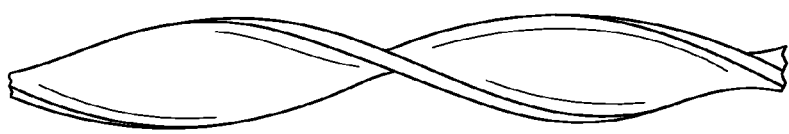
FIGS. 5(*a*) to 5(*d*) are views in perspective of 4 different types of swirl tube inserts.
Figure 5B:
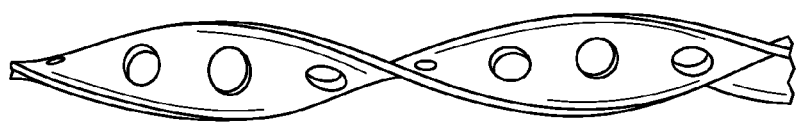
Figure 5C:
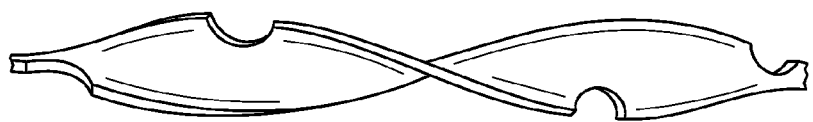
Figure 5D:
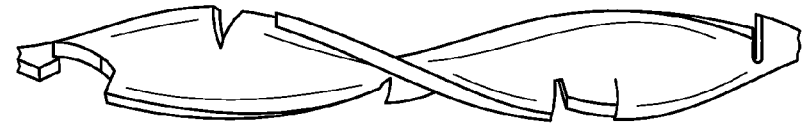

Instead of a wire wrapped displacement insert, a static mixer insert having the geometry shown in FIG. 4 could be utilized. Static mixers are operative to transport, by their mechanical construction, the fluid at the tube wall to the center of the tube and to fold these transported regions of fluid into each other. This dramatically increases heat transfer because it increases the local temperature difference between portions of the bulk (tubeside) fluid and the tube wall. Static mixers are particularly useful in a flow that is laminarized.

Alternatively, a swirl flow tube insert such as the twisted tape swirl inserts shown in FIGS. 5(a)-5(d) could be employed, if so desired. Twisted tapes impart rotational flow which has two effects. It imparts a helical flow path along the inside wall of the tube, thereby producing a high velocity along the tube wall that is a function of the helical flow angle. It also imparts a combination of flow rotation and centripetal force away from the center of the tube that in single-phase flow, increases mixing and turbulence at the tube wall. This creates turbulent flows at Reynolds numbers that would be characteristic of laminar or transition flows in tubes without inserts. Inducing turbulence at a lower Reynolds number enhances heat transfer.

In operation, a stream 100 of aqueous formaldehyde is fed to system 10 via reaction tube 12 of bank S1 along with potassium hydroxide and n-butyraldehyde via a feed port 101. Tube 12 has a tube insert as discussed in connection with FIGS. 2 and 3. After passing through tube 12, the reaction mixture proceeds through additional tubes in bank S1 where the reaction proceeds and stream 100 becomes enriched in methylolated product before being passed to the next stage of the system.

Additional potassium hydroxide and n-butyraldehyde is provided to stream 100 via another feed port 102 as the stream is fed to reactor stage S2 wherein the first tube is provided with a tube insert as discussed above. Stream 100 proceeds through the tubes of stage S2 such as tube 14 before exiting the stage.

The outlet of bank S2 is optionally provided with cooler 35 to further regulate temperature in the system.

After exiting bank S2 and cooler 35, stream 100 is provided with additional butyraldehyde and potassium hydroxide at a feed port indicated at 103 and fed to reactor tube bank S3 as shown. The first tube of bank S3 is likewise provided with a tube insert, whereas the subsequent tubes of the bank need not have inserts.

Stream 100 is passed through the tubes of bank S3 and thereafter still additional butyraldehyde and potassium hydroxide may be added in subsequent stages if so desired, or the stream may be provided to additional reactor banks without further providing reactants.

During operation of system 10 as described above, the temperature in the reaction tubes is regulated independently in the various reaction tube banks by way of a plurality of temperature indicator controllers (TIC's), control valves and one or more coolers such as cooler 35. Generally, the temperature in the reaction medium is maintained between 35° C. and 75° C. Preferably, the temperature in the reaction medium is maintained at between 35° C. and 65° C. at all times and temperature spikes are minimized or eliminated.

To this end, coolant feed 20 is pumped to reactor banks S1, S2 and S3 such that the coolant circulates through the annular cooling channels of the reaction tubes before returning to the coolant system via return lines 22. TIC controllers sense the temperature of the coolant and regulate control valves in order to maintain a target temperature of the coolant thus maintaining a target temperature of the reaction medium as well. The controllers and valves are configured such that the temperature of each stage can be independently controlled.

TIC's 24, 26, 30 sense the reaction temperature in banks S1, S2 and S3 and regulate the flow of the coolant through valves 40, 42, 46 in order to maintain target reaction temperatures in the banks. Another TIC 28 senses temperature in cooler 35 and controls coolant flow via valve 44 to further adjust temperatures in the system.

The inventive system may be sized and operated in a variety of operating modes wherein reactants and catalyst are added in stages to minimize temperature spikes and maintain target temperatures.

The amount of reactants employed will vary depending upon the process employed and the products made; for example, the aggregate formaldehyde: $C_2$ and higher aldehyde reactant mole ratio differs with the $C_2$ and higher aldehyde reactant. If a Cannizzaro reaction scheme is included, acetaldehyde requires a minimum of ratio of formaldehyde: acetaldehyde of 4:1, n-butyraldehyde requires a minimum of ratio of formaldehyde:n-butyraldehyde of 3:1, and isobutyraldehyde requires a minimum of ratio of formaldehyde: isobutyraldehyde of 2:1. For n-butyraldehyde recommended ranges of formaldehyde: butyraldehyde are from 3.01:1 to 10:1.

A set of preferred operating parameters for making TMP from n-butyraldehyde in a Cannizzarro process are as follows:

| | |
|---|---|
| Reaction Medium Temperature | 35° C.-65° C. |
| Aqueous Formaldehyde Concentration (wt % Formaldehyde) | 10%-50% |
| Aggregate Formaldehyde/Reactant Aldehyde Molar Ratio | 3.01:1-10:1 |
| Aggregate Inorganic Base/Reactant Aldehyde Molar Ratio | 1:1-2:1 preferably 1:1-1.5:1 |

Introducing the aldehyde in increments raises the effective formaldehyde/reactant aldehyde ratio and reduces the formation of dimers through self-condensation of the $C_2$ or higher condensable aldehyde. So also, staged addition of base lowers the base/formaldehyde ratio in the initial stages and reduces methanol generation in connection with a Cannizzaro process. Various operating schemes include the schemes (a), (b) and (c):

(a) Wherein the $C_2$ or higher condensible aldehyde is added in a fixed proportion with inorganic base at said plurality of successive feed points to provide a production stream which is progressively provided with additional $C_2$ or higher condensible aldehyde as the production stream advances through the successive reaction stages;

(b) Wherein the $C_2$ or higher condensible aldehyde and inorganic base are provided in an upstream feed point in larger amounts relative to amounts provided in a downstream feed point. Providing larger portions of reactants in early stages provides additional residence time and is desirable if adequate cooling is available in the system. One preferred protocol in a Cannizzaro process is to provide 30-60% of the aggregate amount of both the base and the $C_2$ or higher condensible aldehyde in early reaction stage(s);

(c) Wherein the inorganic base is provided in a downstream feed point in a larger amount relative to an amount provided in an upstream feed point to provide a production stream which is provided with inorganic base at higher levels in a later stage as compared with levels of inorganic base in an initial stage.

Said process options may include the option of using different ratios of base and condensable aldehyde along the feeding points, as long as the total of all additions equals the targeted component ratios.

After the production stream 100 exits the last bank of the reaction system, further work-up includes extracting formates from the reclaimed TMP and distillation of the crude TMP to purified form as is known in the art. Typically, purification of the crude product includes a multistage water/ethyl acetate extraction system, as well as one or more distillation tower (s).

The process and apparatus of the present invention are especially suited to the inorganic Cannizzaro process of the class described in U.S. Pat. Nos. 3,183,274, 5,948,943, 7,253,326 and 8,354,561 referred to above. Alternatively, the apparatus and process methodology could be employed in connection with an organic Cannizzaro process or a condensation/hydrogenation methylolalkane process described in U.S. Pat. No. 7,301,058.

There is thus provided in accordance with the present invention a method of making a methylolalkane from formaldehyde and a $C_2$ or higher condensable aldehyde in a multistage process comprising: (a) providing a formaldehyde containing stream to a tubular reaction system with a plurality of successive reaction stages; (b) adding a $C_2$ or higher condensible aldehyde and optionally a base to the formaldehyde containing stream wherein at least one of the $C_2$ or higher condensible aldehyde or base are added to the formaldehyde containing stream at a plurality of successive feed points to provide a production stream which is progressively provided with additional $C_2$ or higher condensible aldehyde or base as the production stream advances through the successive reaction stages; and (c) converting the $C_2$ or higher condensible aldehyde and formaldehyde to a methylolalkane.

The $C_2$ or higher condensible aldehyde may be added to the formaldehyde containing stream at a plurality of successive feed points to provide a production stream which is progressively provided with additional $C_2$ or higher condensible aldehyde as the production stream advances through the successive reaction stages.

In various methods of the invention, the methylolalkane may be pentaerythritol and the $C_2$ or higher condensible aldehyde is acetaldehyde or the methylolalkane is trimethylolethane and the $C_2$ or higher condensible aldehyde is propionaldehyde. Likewise, the methylolalkane may be trimethylolpropane and the $C_2$ or higher condensible aldehyde is n-butyraldehyde or the methylolalkane may be neopentyl glycol and the $C_2$ or higher condensible aldehyde is isobutyraldehyde.

The base may be added to the formaldehyde containing stream at a plurality of successive feed points to provide a production stream which is progressively provided with additional base as the production stream advances through the successive reaction stages if so desired or both the $C_2$ or higher condensible aldehyde and an inorganic base may be added to the formaldehyde containing stream at a plurality of successive feed points to provide a production stream which is progressively provided with additional $C_2$ or higher condensible aldehyde and inorganic base as the production stream advances through the successive reaction stages.

Throughout the various aspects of the invention, an inorganic base selected from potassium hydroxide, calcium hydroxide and sodium hydroxide may be employed.

Preferably, the inorganic base and $C_2$ or higher condensible aldehyde is added to the production stream in at least 3 discrete locations and in some cases in at least 4 discrete locations.

While different numbers of stages may be employed, preferably the tubular reaction system has at least 3 stages.

Typically, the temperature of the production stream is maintained between 30° C. and 75° C.; more preferably in many cases the temperature of the production stream is maintained between 35° C. and 65° C.

In some embodiments, said $C_2$ or higher condensible aldehyde is added in a fixed proportion with inorganic base at said plurality of successive feed points to provide a production stream which is progressively provided with additional $C_2$ or higher condensible aldehyde as the production stream advances through the successive reaction stages. In still other embodiments, said $C_2$ or higher condensible aldehyde and inorganic base are provided in an upstream feed point in larger amounts relative to amounts provided in a downstream feed point.

In still other cases, the inorganic base is provided in a downstream feed point in a larger amount relative to an amount provided in an upstream feed point to provide a production stream which is provided with inorganic base at higher levels in a later stage as compared with levels of inorganic base in an initial stage.

In another aspect of the invention, there is provided a multistage tubular reaction system for preparing methylol derivatives of a $C_2$ or higher condensible aldehyde comprising: (a) a tubular reaction system with a plurality of successive reactor stages comprising a plurality of reaction tubes; (b) a reaction system inlet adapted to provide a formaldehyde containing stream to the tubular reaction system; and (c) a plurality of feed ports adapted to provide at least one of the $C_2$ or higher condensible aldehyde or a base to the formaldehyde containing stream at a plurality of successive feed points to provide a production stream which is progressively provided with additional $C_2$ or higher condensible aldehyde or base as the production stream advances through successive reaction stages. The multistage tubular reaction system is preferably adapted to provide both $C_2$ or higher condensible aldehyde and base to the successive stages of the reaction system such that the production stream is progressively provided with additional $C_2$ or higher condensible aldehyde and base as the production stream advances through successive reaction stages.

While the invention has been described in detail, modifications within the spirit and scope of the invention will be readily apparent to those of skill in the art. Such modifications are also to be considered as part of the present invention. In view of the foregoing discussion, relevant knowledge in the art and references discussed above in connection with the Background of the Invention, the Summary of Invention and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A method of making a methylolalkane from formaldehyde and a $C_2$ or higher condensable aldehyde in a multistage process comprising:
   (a) providing a formaldehyde containing stream to a tubular reaction system with a plurality of successive reaction stages;
   (b) adding a $C_2$ or higher condensible aldehyde and optionally a base to the formaldehyde containing stream wherein at least one of the $C_2$ or higher condensible aldehyde or base are added to the formaldehyde containing stream at a plurality of successive feed points to provide a production stream which is progressively provided with additional $C_2$ or higher condensible aldehyde or base as the production stream advances through the successive reaction stages; and (c) converting the $C_2$ or higher condensible aldehyde and formaldehyde to a methylolalkane.

2. The method according to claim 1, wherein the $C_2$ or higher condensible aldehyde is added to the formaldehyde containing stream at a plurality of successive feed points to provide a production stream which is progressively provided with additional $C_2$ or higher condensible aldehyde as the production stream advances through the successive reaction stages.

3. The method according to claim 1, wherein the methylolalkane is trimethylolpropane and the $C_2$ or higher condensible aldehyde is n-butyraldehyde.

4. The method according to claim 1, wherein the methylolalkane is neopentyl glycol and the $C_2$ or higher condensible aldehyde is isobutyraldehyde.

5. The method according to claim 1, wherein base is added to the formaldehyde containing stream at a plurality of successive feed points to provide a production stream which is progressively provided with additional base as the production stream advances through the successive reaction stages.

6. The method according to claim 5, wherein said base is an inorganic base selected from potassium hydroxide, calcium hydroxide and sodium hydroxide.

7. The method according to claim 1, wherein said tubular reaction system has at least 3 stages.

8. The method according to claim 1, comprising adding the $C_2$ or higher condensible aldehyde and an inorganic base to the formaldehyde containing stream at a plurality of successive feed points to provide a production stream which is progressively provided with additional $C_2$ or higher condensible aldehyde and inorganic base as the production stream advances through the successive reaction stages.

9. The method according to claims 8, wherein said inorganic base is selected from potassium hydroxide, calcium hydroxide and sodium hydroxide.

10. The method according to claim 8, wherein said $C_2$ or higher condensible aldehyde is added in a fixed proportion with inorganic base at said plurality of successive feed points to provide a production stream which is progressively provided with additional $C_2$ or higher condensible aldehyde as the production stream advances through the successive reaction stages.

11. The method according to claim 10, wherein said $C_2$ or higher condensible aldehyde and inorganic base are provided in an upstream feed point in larger amounts relative to amounts provided in a downstream feed point.

12. The method according to claim 8, wherein said inorganic base is provided in a downstream feed point in a larger amount relative to an amount provided in an upstream feed point to provide a production stream which is provided with inorganic base at higher levels in a later stage as compared with levels of inorganic base in an stage.

13. The method according to claim 1, wherein the temperature of the production stream is maintained between 30° C. and 75° C.

14. A multistage tubular reaction system for preparing methylol derivatives of a $C_2$ or higher condensible aldehyde comprising:
(a) a tubular reaction system with a plurality of successive reactor stages comprising a plurality of reaction tubes cooled with a coolant in order to maintain a desired temperature;
(b) a reaction system inlet adapted to provide a formaldehyde containing stream to the tubular reaction system; and
(c) a plurality of feed ports adapted to provide at least one of the $C_2$ or higher condensible aldehyde or a base to the formaldehyde containing stream at a plurality of successive feed points to provide a production stream which is progressively provided with additional $C_2$ or higher condensible aldehyde or base as the production stream advances through successive reaction stages,
wherein the temperature of the production stream is maintained between 30° C. and 75° C.

15. The multistage tubular reaction system for preparing methylol derivatives of a $C_2$ or higher condensible aldehyde according to claim 14, wherein the reaction system comprises a plurality of reaction tubes of a jacketed construction with an outer shell, an annular cooling channel and an inner reaction tube defining a reaction zone and wherein the annular cooling channel receives coolant.

16. A multistage tubular reaction system for preparing methylol derivatives of a $C_2$ or higher condensible aldehyde comprising:
(a) a tubular reaction system with a plurality of successive reactor stages comprising a plurality of reaction tubes cooled with a coolant in order to maintain a desired temperature;
(b) a reaction system inlet adapted to provide a formaldehyde containing stream to the tubular reaction system; and
(c) a plurality of feed ports adapted to provide at least one of the $C_2$ or higher condensible aldehyde or a base to the formaldehyde containing stream at a plurality of successive feed points to provide a production stream which is progressively provided with additional $C_2$ or higher condensible aldehyde or base as the production stream advances through successive reaction stages,
wherein the reaction system comprises a plurality of reaction tubes of a jacketed construction with an outer shell, an annular cooling channel and an inner reaction tube defining a reaction zone and wherein the annular cooling channel receives coolant.

* * * * *